US011825818B2

(12) United States Patent
Kim et al.

(10) Patent No.: US 11,825,818 B2
(45) Date of Patent: Nov. 28, 2023

(54) METHOD FOR PREPARING A LARGE ANIMAL MODEL WITH PERITONEAL CARCINOMATOSIS

(71) Applicants: SEOUL NATIONAL UNIVERSITY HOSPITAL, Seoul (KR); SEOUL NATIONAL UNIVERSITY R&DB FOUNDATION, Seoul (KR); THE CATHOLIC UNIVERSITY OF KOREA INDUSTRY-ACADEMIC COOPERATION FOUNDATION, Seoul (KR)

(72) Inventors: Hee Seung Kim, Seoul (KR); Jeong Mook Lim, Seoul (KR); Ji Yeon Ahn, Seoul (KR); Na Ra Lee, Seoul (KR); Eun Ji Lee, Seoul (KR); Soo Jin Park, Seoul (KR); Sung Jong Lee, Seoul (KR)

( * ) Notice: Subject to any disclaimer, the term of this patent is extended or adjusted under 35 U.S.C. 154(b) by 272 days.

(21) Appl. No.: 16/846,321

(22) Filed: Apr. 11, 2020

(65) Prior Publication Data

US 2021/0051926 A1 Feb. 25, 2021

(30) Foreign Application Priority Data

Aug. 19, 2019 (KR) ........................ 10-2019-0100793

(51) Int. Cl.
*A01K 67/027* (2006.01)
(52) U.S. Cl.
CPC ...... *A01K 67/0271* (2013.01); *A01K 2207/12* (2013.01); *A01K 2227/108* (2013.01); *A01K 2267/0331* (2013.01)
(58) Field of Classification Search
None
See application file for complete search history.

(56) References Cited

PUBLICATIONS

Kim et al JSOG Congress Award Oncology, abstract, p. 1 (Year: 2019).*
Salmon Reprod Nutr Dev. ; 24(2):197-206, abstract. (Year: 1984).*
Reymond et al European Journal of Surgical Oncology, 26: 393-397 (Year: 2000).*
Mei et al. BMC Cancer, 10:124, 1-8 (Year: 2010).*
Boettcher et al Pigs Front. Oncol. 2019, 9, 9, 1-7, (Year: 2019).*
Yao et al Oncology Lattes , 10, 3450-3456). (Year: 2015).*
Birteeb et al Research & Reviews: Journal of Veterinary Science and Technology, 4, 3, ; 15-23 (Year: 2015).*
Perkins et al Scientific Reports, 8930, 1-10). (Year: 2018).*
Yang-Hartwich et al Science Report, 4:6116, 1-12 (Year: 2014).*
Lee et al Journal of Translational Medicine 20:329, 1-12 (Year: 2022).*
Kim et al., 2019, JSOG Congress Award Candidate 5 Oncology 2 (Group 5).
Schorge et al., Surgical Debulking of Ovarian Cancer: What Difference Does It Male?, Nov. 3, 2010, Rev Obstet Gynecol, 3:111-117.
Coccolini et al., Peritoneal carcinomatosis, Nov. 7, 2013, World J Gastroenterol, 19: 6979-6994.
Sugarbaker et al., Results of Treatment of 385 Patients With Peritoneal Surface Spread of Appendiceal Malignancy, 1999, Ann Surg Oncol, 6: 727-731.
van Driel et al., Hyperthermic Intraperitoneal Chemotherapy in Ovarian Cancer, Jan. 18, 2018, N Engl J Med, 378: 230-240.
Verwaal et al., Randomized Trial of Cytoreduction and Hyperthermic Intraperitoneal Chemotherapy Versus Systemic Chemotherapy and Palliative Surgery in Patients With Peritoneal Carcinomatosis of Colorectal Cancer, Oct. 13, 2003, J Clin Oncol, 21: 3737-3743.
Verwaal et al., 8-Year Follow-up of Randomized Trial: Cytoreduction and Hyperthermic Intraperitoneal Chemotherapy Versus Systemic Chemotherapy in Patients with Peritoneal Carcinomatosis of Colorectal Cancer, 2008, Ann Surg Oncol, 15: 2426-2432.
Cao et al., A Systematic Review and Meta-Analysis of Cytoreductive Surgery with Perioperative Intraperitoneal Chemotherapy for Peritoneal Carcinomatosis of Colorectal Origin, 2009, Ann Surg Oncol, 16: 2152-2165.
Biores Open Access. vol. 1 No. 2 pp. 63-68, 2012.
Int J Clin Exp Pathol vol. 9 No. 7 pp. 6835-6845, 2016.
Int J Gynecol Cancer vol. 17 No. 2 pp. 407-147, 2007.
J Surg Oncol. vol. 109 No. 2 pp. 110-116, 2014.
Korean J Clin Oncol. 2010;6(1) 4-6 & Its English Abstract.
Surg Endosc, vol. 30(10), pp. 4258-4264, 2016.
KR Decision to Grant dated Mar. 29, 2021.

* cited by examiner

*Primary Examiner* — Anoop K Singh
(74) *Attorney, Agent, or Firm* — Harvest IP Law, LLP

(57) ABSTRACT

The present invention relates to a method for preparing a large animal model, with peritoneal carcinomatosis, which is an abdominal cavity metastasis of tumor commonly found in advanced or recurrent solid cancer, is induced using a large animal, and the method for preparing a large animal model with peritoneal carcinomatosis comprises injecting a cancer cell line into the abdominal cavity of a piglet in which the immune function is not completed. The method for preparing a large animal model with peritoneal carcinomatosis, when a human-derived immortalized cell line is inoculated into a pig, can overcome xenograft rejection and induce peritoneal carcinomatosis, can use animals with sufficient supply and demand, and can expect the spread of peritoneal carcinomatosis through breeding.

3 Claims, 12 Drawing Sheets

(A)

(B)

(C)

(A)

(B)

(C)

(A)

(B)

(C)

(A)

(B)

(C)

(A)

(B)

(C)

(D)

(E)

(A)

(B)

(C)

METHOD FOR PREPARING A LARGE ANIMAL MODEL WITH PERITONEAL CARCINOMATOSIS

BACKGROUND OF THE INVENTION

Field of the Invention

The present invention relates to a method for preparing a large animal model, in which peritoneal carcinomatosis, which is an abdominal cavity metastasis of tumor commonly found in advanced or recurrent solid cancer, is induced using a large animal.

The large animal model can be used in non-clinical studies to evaluate the efficacy and safety of anticancer drugs, targeted drugs, and cancer immunotherapy for advanced or recurrent solid cancer, and can be used in non-clinical studies to evaluate surgeries and new medical technologies using medical devices for treating advanced or recurrent solid cancer.

Related Art

Peritoneal carcinomatosis (hereinafter, PC) is a cancer metastasis commonly confirmed in advanced or recurrent solid cancer. In particular, PC is found in almost all of advanced ovarian cancer and in 15% of patients with rectal cancer, which has a fatal effect on prognosis (Schorge et al., 2010, Rev Obstet Gynecol, 3: 111-117; Coccolini et al., 2013, World J Gastroenterol, 19: 6979-6994). Patients with PC typically have a very poor prognosis and suffer from numerous complications of the disease, including advanced intestinal obstruction. The optimal treatment is cytoreductive surgery (hereinafter, CRS) with accompanying hyperthermic intraperitoneal chemotherapy (hereinafter, HIPEC). However, the CRS-HIPEC treatment has been used with moderate success in highly selected patients with a limited disease burden.

During the CRS-HIPEC therapy, all the tumors in the visible abdominal cavity should be debulked, and then microscopic residual tumors are treated with locally-delivered intraperitoneal chemotherapy. In particular, HIPEC therapy is most effective when the tumor burden is low after removing any tumor nodules greater than 2.5 mm with CRS treatment. The results vary depending on the tumor grade, where the 5-year survival rate of a low grade tumor is in a range of 63% to 100% and the 5-year survival rate of a high grade tumor is in a range of 0% to 65% (Sugarbaker et al., 1999, Ann Surg Oncol, 6: 727-731).

Reviewing the results of phase 3 clinical trial, it was confirmed that the CRS-HIPEC treatment, compared to systemic chemotherapy, has a significantly improved survival rate in PC patients with ovarian cancer and rectal cancer (van Driel et al., 2018, N Engl J Med, 378: 230-240; Verwaal et al., 2003, J Clin Oncol, 21: 3737-3743; Verwaal et al., 2008, Ann Surg Oncol, 15: 2426-2432). Certainly, most PC patients are not subjects for CRS-HIPEC treatment and are repeatedly treated with systemic chemotherapy and allow a further progress of the disease ultimately leading to death (Coccolini et al., 2013, World J Gastroenterol, 19: 6979-6994; Cao et al., 2009, Ann Surg Oncol, 16: 2152-2165), whereas the therapy for tumor reduction via CRS treatment and topical drug delivery via HIPEC treatment is very important in addressing the unmet clinical need to improve the therapeutic effect of PC patients with poor prognosis.

Meanwhile, the existing peritoneal carcinomatosis animal models for carcinomatosis study were mostly performed using nude mice, which are relatively expensive immunosuppressive small animals, and even when an animal model was developed, it was too small to evaluate the response by the intravenous treatment or intraperitoneal treatment. Additionally, there is absolutely no large animal model of peritoneal carcinomatosis in which peritoneal carcinomatosis, which is a characteristic of advanced solid cancer occurring in the human body, can be similarly reproduced and the evaluation of a response after intravenous treatment and intraperitoneal treatment can be performed as in the human body.

RELATED LITERATURE

Schorge et al., 2010, Rev Obstet Gynecol, 3:111-117
Coccolini et al., 2013, World J Gastroenterol, 19: 6979-6994
Sugarbaker et al., 1999, Ann Surg Oncol, 6: 727-731
van Driel et al., 2018, N Engl J Med, 378: 230-240
Verwaal et al., 2003, J Clin Oncol, 21: 3737-3743
Verwaal et al., 2008, Ann Surg Oncol, 15: 2426-2432
Coccolini et al., 2013, World J Gastroenterol, 19: 6979-6994
Cao et al., 2009, Ann Surg Oncol, 16: 2152-2165

SUMMARY OF THE INVENTION

An object of the present invention is to provide a method for preparing a large animal model with peritoneal carcinomatosis, which, when a human-derived immortalized cell line is inoculated into a pig, can overcome xenograft rejection and induce peritoneal carcinomatosis, can use animals with sufficient supply and demand, and can expect the spread of peritoneal carcinomatosis through breeding.

According to an embodiment of the present invention, there is provided a method for preparing a large animal model with peritoneal carcinomatosis, which includes injecting a cancer cell line into the abdominal cavity at a position of the abdominal cavity of a piglet in which the immune function is not completed.

The cancer cell line may be a human ovarian cancer cell line.

The piglet in which the immune function is not completed may be a 3- to 8-week-old pig with a body weight of 6 kg to 15 kg.

The position where the cancer cell line is injected into the abdominal cavity may be any one position selected from the group consisting of the omentum, peritoneum, uterine horn, and a combination thereof.

The position where the cancer cell line is injected into the abdominal cavity may be the uterine horn.

The method for preparing a large animal model with peritoneal carcinomatosis may further include injecting the cancer cell line at a concentration in a range of $0.1 \times 10^6$ cells/0.1 mL to $100.0 \times 10^6$ cells/0.1 mL.

The cancer cell line may be injected into the abdominal cavity using laparoscopy.

The method for preparing a large animal model with peritoneal carcinomatosis, one to two weeks after the injection of the cancer cell line into the abdominal cavity, may further include a secondary injection of the cancer cell line at the same position of the abdominal cavity.

The success rate for making a large animal model with peritoneal carcinomatosis after the injection of the cancer cell line by using this present invention may be 70% and more.

DESCRIPTION OF EXEMPLARY EMBODIMENTS

Figure 1:
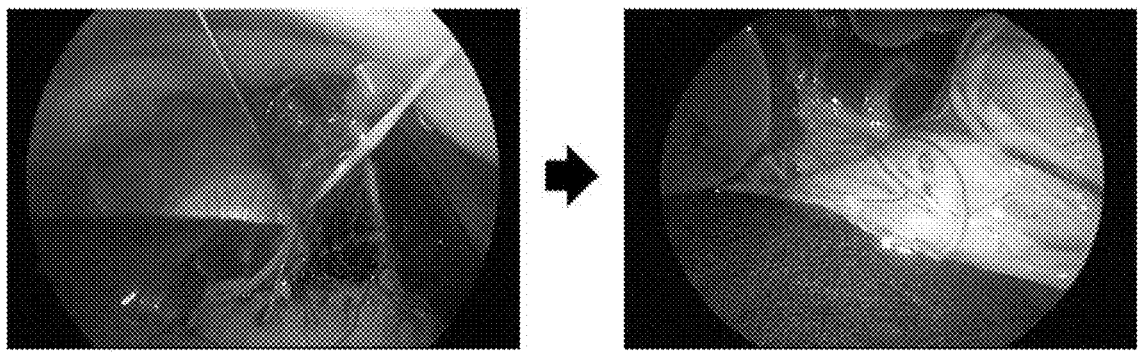
FIG. 1 shows the images of (A) the omentum, (B) the peritoneum, and (C) the uterine horn of a piglet at the time of the injection of an ovarian cancer cell line (SK-OV-3) thereinto (left); and the images of (A) the omentum, (B) the peritoneum, and (C) the uterine horn of the piglet two weeks after the injection (right), respectively.
Figure 1:
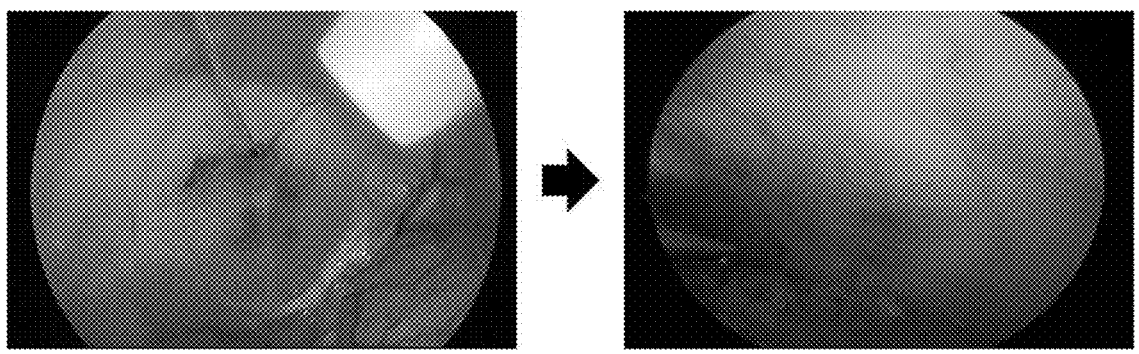
Figure 1:
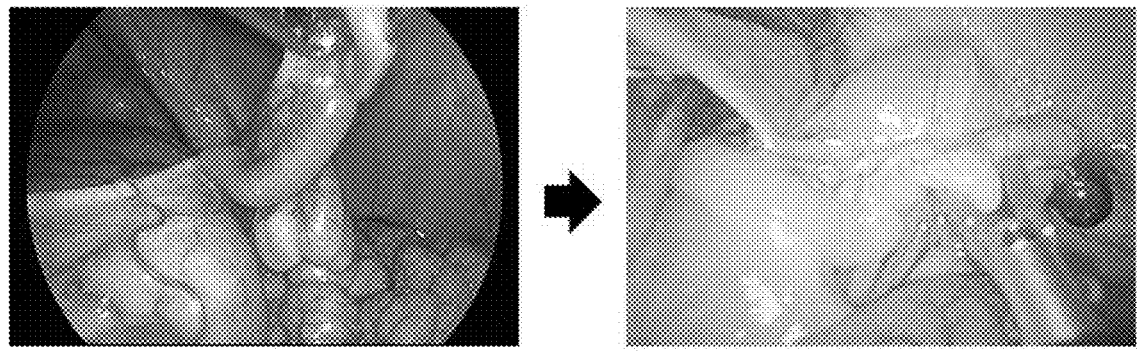

Hereinafter, the present invention will be described in more detail.

As used herein, the term "animal model" or "large animal model" refers to a non-human animal model or a large non-human animal model excluding humans.

As used herein, the term "cell", "cell line", and "cell culture" are used interchangeably, including their offspring. Accordingly, the term "cell" includes the main subject cells and cultures derived therefrom, regardless of the number to be delivered, and also includes progeny having the same function or biological activity.

As used herein, the term "tumor" refers to all neoplastic cell growth and proliferation and all precancerous and cancerous cells and tissues, whether malignant or benign.

As used herein, the terms "cancer" and "cancerous" refer to or describe a physiological condition in a mammal which is typically characterized by an unregulated cell growth.

Examples of cancer include carcinoma, lymphoma, blastoma, sarcoma, and leukemia or malignant tumor, but cancer is not limited thereto. More specific examples of these cancers include squamous cell carcinoma (e.g., epithelial squamous cell carcinoma), lung cancer including small cell lung cancer, non-small cell lung cancer, adenocarcinoma of the lung, and squamous carcinoma of the lung, peritoneum cancer, hepatocellular carcinoma, gastric cancer including gastrointestinal cancer or stomach cancer, pancreatic cancer, glioblastoma, uterine cervical cancer, ovarian cancer, liver cancer, bladder cancer, hepatocellular carcinoma, breast cancer, colon cancer, rectal cancer, colorectal cancer, endometrial or uterine carcinoma, salivary gland carcinoma, kidney or renal cell cancer, prostate cancer, vulva cancer, thyroid cancer, liver carcinoma, anal carcinoma, penile carcinoma, and head and neck cancer.

The method for preparing a large animal model with peritoneal carcinomatosis according to an embodiment of the present invention includes injecting a cancer cell line into the abdominal cavity of a piglet, in which the immune function is not completed.

The method for preparing a large animal model with peritoneal carcinomatosis is to induce peritoneal carcinomatosis, which is the abdominal cavity metastasis of tumor commonly found in advanced or recurrent solid cancer, using a large animal model. In the method for preparing a large animal model with peritoneal carcinomatosis, when a human-derived immortalized cell line is inoculated into a pig, selection of an appropriate large animal, control of the culture conditions for a cancer cell line, an injection technology for a cancer cell line, and the position for injection location of a cancer cell line are important, so as to overcome xenograft rejection and induce peritoneal carcinomatosis First, the things to consider when selecting a large animal to induce peritoneal carcinomatosis are that the immune function should not be completed in the large animal and that the large animal itself should be able to take care of its own regimen without any complication after the surgery of cancer cell line metastasis.

Considering the above things, as the large animal, a 3- to 8-week-old piglet with a body weight of 6 kg to 15 kg, and preferably a 4- to 7-week-old piglet with a body weight of 7 kg to 8 kg in which the immune function is not completed may be used. When the piglet is less than 3 week old, it may be difficult to breed the piglet because the piglet may lack the immune function and the ability to control its regimen, whereas when the piglet is more than 8 week old, the engraftment of a cancer cell line may be difficult because the immune function is completed in the piglet.

In the past, small animals in which immunosuppression was induced were used to prepare an animal model and thus the costs for purchase and maintenance were significant. However, the present invention employs natural piglets in which the immunity is immature using the natural pigs, the supply and demand of animals is sufficient the spread of peritoneal carcinomatosis through breeding can be expected.

Additionally, when a large animal model with peritoneal carcinomatosis is prepared using a pig growing by 1 kg per week, peritoneal carcinomatosis, which shows a multiple tumor spread in advanced solid cancer when the body weight is between about 15 kg and about 20 kg, can be confirmed. Therefore, for the pig, being a large animal most closest to humans, the treatment response can be analyzed by administering a drug via intravenous chemotherapy and intraperitoneal chemotherapy as in humans, even in a case where a cancer cell line derived from a human body is used as the cancer cell line, instead of evaluating the treatment response by injecting a drug directly into the tumor or inducing a modification in the tumor growth environment as it has been performed previously, and it can also be used for the evaluation of a new medical technology using a surgery and medical device for the solid cancer of peritoneal carcinomatosis with a size comparable to that of humans.

The cancer cell line can be any cancer cell line that can cause peritoneal carcinomatosis.

In an embodiment, the cancer cell line may be any one selected from the group consisting of a kidney cancer cell line (e.g., RENCA), a stomach cancer cell line, a brain cancer cell line, a lung cancer cell line, a breast cancer cell line, an ovarian cancer cell line, a liver cancer cell line, a bronchial cancer cell line, a nasopharyngeal cancer cell line, a laryngeal cancer cell line, a pancreas cancer cell line, a bladder cancer cell line, a colon cell line, and a cervical cancer cell line.

Specifically, it is preferable to use a human ovarian cancer cell line as the cancer cell line, considering the biological characteristics that peritoneal carcinomatosis is accompanied in most cases during the progress of ovarian cancer and thus it is easy to induce peritoneal carcinomatosis compared to other cancer cell lines. In an embodiment, as the human ovarian cancer cell line, SK-OV-3 and SNU-008 cell lines, which can be purchased from the Korean Cell Line Bank (KCLB), may be used.

The method for preparing the large animal model with peritoneal carcinomatosis may further include injecting the cancer cell line at a concentration of $0.1 \times 10^6$ cells/0.1 mL to $100.0 \times 10^6$ cells/0.1 mL, and preferably at a concentration of $5.0 \times 10^6$ cells/0.1 mL to $10.0 \times 10^6$ cells/0.1 mL.

When the concentration of the cancer cell line is lower than $0.1 \times 10^6$ cells/0.1 mL, it may not be possible for the injection to maintain a proper number of cells for implantation after dispersion because there are few cells, whereas when the concentration of the cancer cell line is greater than $100.0 \times 10^6$ cells/0.1 mL, necrosis and fallout may occur before implantation due to overproliferation.

As the medium for culturing the cancer cell line, any cell culture medium commonly used, for example, Roswell Park Memorial Institute 1640 (RPMI 1640), Dulbecco's Modified Eagle's Medium (DMEM), alpha-Minimum Essential Medium (α-MEM), McCoy's 5A medium, Eagle's basal medium, Connaugh Medical Research Laboratories 1066 (CMRL 1066), Glasgow minimum essential medium, Ham's nutrient mixtures medium, Iscove's Modified Dulbecco's Medium (IMDM), and Liebovitz' L-15 medium are all possible.

Additionally, at least one supplementary ingredient may be added to the medium as needed, and along with the sera from fetal calves, horses, humans, etc., at least one selected from components in serum or plasma such as albumin, dextran 40, injection solutions such as physiological saline, antibiotics such as penicillin G, streptomycin sulfate, gentamicin, etc., and antifungal agents such as amphotericin B, nystatin, etc. to prevent microbial contamination may be used.

The cultured cancer cell line is injected into a specific anatomical position inside the pig's abdominal cavity, which requires an invasive procedure.

Conventionally, the method of percutaneous injection was used in the case of a small animal, and injection through skin incision was attempted in the case of a large animal. In the present invention, since a pig having the abdominal cavity structure similar to the human body is used as a subject, the cancer cell line can be injected exactly at the targeted anatomical position using laparoscopy.

The anatomical location inside the abdominal cavity where the cancer cell line is injected, considering the anatomical position of the human body where the peritoneal carcinomatosis proceeds first, may be any one position selected from the group consisting of the omentum, the peritoneum, the uterine horn, and the combination thereof, and the cancer cell line may be injected into the uterine horn considering the primary site.

In the case of the omentum and the peritoneum of the pig, after the cancer cell line is injected, the cell line spreads to surrounding tissues, thereby reducing the cell line that can induce a reaction with tissues. In contrast, the pig's womb is in the form of a soft tube like the fallopian tube of the human body, and when the cancer cell line is injected into the uterine horn, the end of the uterus is maintained in the form of a bottleneck as the tube end is swollen, and thus the conditions in which the cancer cell line injected into the tube can continuously react with epithelial cells of the uterus are naturally established.

In an embodiment, FIG. 1 shows the images of (A) the omentum, (B) the peritoneum, and (C) the uterine horn of a piglet at the time of the injection of the ovarian cancer cell line (SK-OV-3) thereinto (left); and the images of (A) the omentum, (B) the peritoneum, and (C) the uterine horn of the piglet two weeks after the injection (right), respectively.

Referring to FIG. 1, it can be seen that the onset of metastasis first begins in the uterus. This is because, in the case of the omentum and peritoneum, the cancer cell line spreads to surrounding tissues, but, in the case of the uterine horn, the cancer cell line continuously reacts with epithelial cells of the uterus, as described above.

Figure 2:
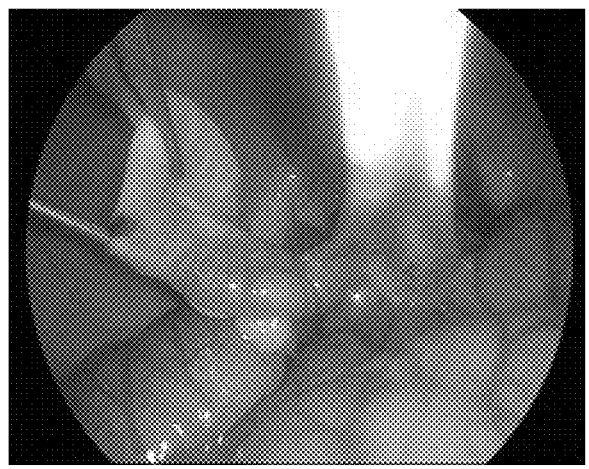
FIG. 2 shows the images of (A) the uterine horn of a piglet at the time when the ovarian cancer cell line (SK-OV-3) was injected only into the uterine horn, (B) the uterine horn of the piglet thereafter with uterine horn tumor formation and adhesion formation, and (C) the uterine horn of the piglet thereafter with occurrence of peritoneal carcinomatosis, respectively.
Figure 2:
Figure 2:
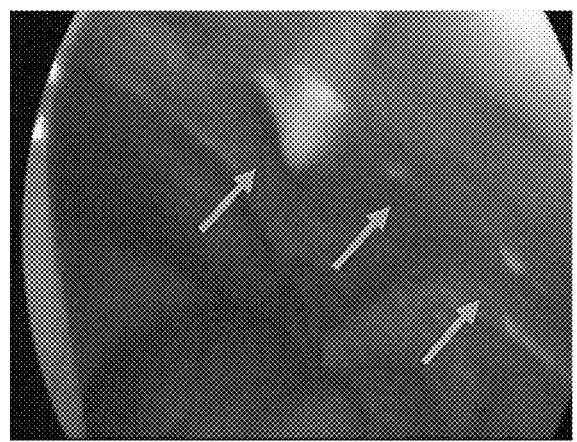

FIG. 2 shows the images of (A) the uterine horn of a piglet at the time when the ovarian cancer cell line (SK-OV-3) was injected only into the uterine horn, (B) the uterine horn of the piglet thereafter with the uterine horn tumor formation and adhesion formation, and (C) the uterine horn of the piglet thereafter with occurrence of peritoneal carcinomatosis, respectively.

Referring to FIG. 2, it can be seen that a large animal model with peritoneal carcinomatosis can be prepared only by injecting the ovarian cancer cell line into the uterine horn.

Meanwhile, to increase the probability of implantation of the injected cancer cell line, the method may further include a step of selectively performing a secondary injection of the cancer cell line. 1571 The secondary injection of the cancer cell line may be performed in the same position one to two weeks after the primary injection.

When the time point for the secondary injection of the cancer cell line is less than one week after the primary injection, the laparoscopy surgery may be performed again in an unrecovered state after laparoscopy surgery, and thus, the implantation may fail due to deterioration of systemic condition and exacerbation of inflammation, whereas when the time point for the secondary injection of the cancer cell line exceeds two weeks, the pig's immune function is completed and thus the probability of implantation may be very low even if an additional cancer cell line is injected.

Additionally, the concentration of the secondary injection of the cancer cell line may be set at $0.1×10^6$ cells/0.1 mL to $100.0×10^6$ cells/0.1 mL, and preferably $5.0×10^6$ cells/0.1 mL to $10.0×10^6$ cells/0.1 mL to be the same as in the primary injection.

The large animal model prepared by the preparation method of a large animal model with peritoneal carcinomatosis is a large animal model closest to the human body, and even in a case where a cancer cell line derived from a human body is used, the treatment response can be analyzed by administering a drug via intravenous chemotherapy and intraperitoneal chemotherapy as in humans, instead of evaluating the treatment response by injecting a drug directly into the tumor or inducing a modification in the tumor growth environment, and it can also be used for the evaluation of a new medical technology using a surgery and medical device for the solid cancer of peritoneal carcinomatosis with a size comparable to that of humans.

The large animal model can be used in non-clinical studies to evaluate the efficacy and safety of anticancer drugs, targeted drugs, and cancer immunotherapy for advanced or recurrent solid cancer, and can be used in non-clinical studies to evaluate surgeries and new medical technologies using medical devices for advanced or recurrent solid cancer.

Hereinafter, Examples of the present invention will be described in detail so that those skilled in the art to which the present invention pertains can easily practice. However, the present invention can be implemented in many different forms and is not limited to the Examples described herein.

Example 1

A human ovarian cancer cell line, SK-OV-3 cell line, was purchased from the Korean Cell Line Bank (KCLB) and cultured in the Mccoy's 5a medium (Welgene, Gyeongsan, Korea) supplemented with 10% heat inactivated fetal bovine serum (FBS, Welgene) and 1% penicillin/streptomycin (Gibco, Gaithersburg, USA).

The cultured cell line was collected in the exponential phase and decomposed into a single-cell suspension, and the suspension concentration of the SK-OV-3 cell line for inoculation was adjusted to $5.0×10^6$ cells/0.1 mL.

Figure 3:
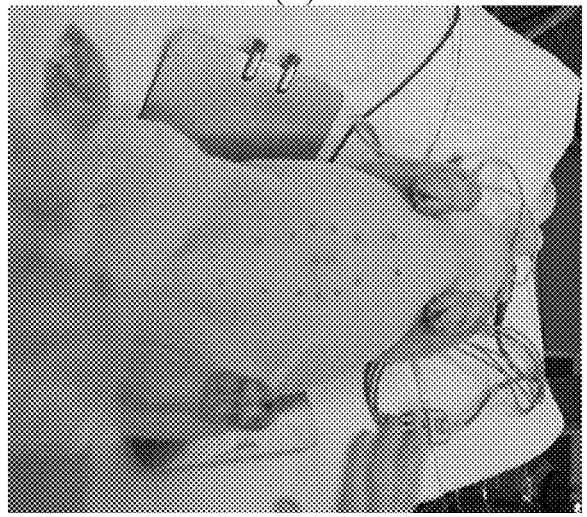
FIG. 3 shows the images of (A) a 4-week-old pig with a body weight of 7 kg, (B) a process of inserting a veress needle into the abdominal wall of the pig and injecting a $CO_2$ gas thereinto, and (C) confirming the abdominal cavity structure of the pig using a laparoscopy camera and a forceps after inserting a 5 mm laparoscopy trocar thereinto in Example 1, respectively.
Figure 3:
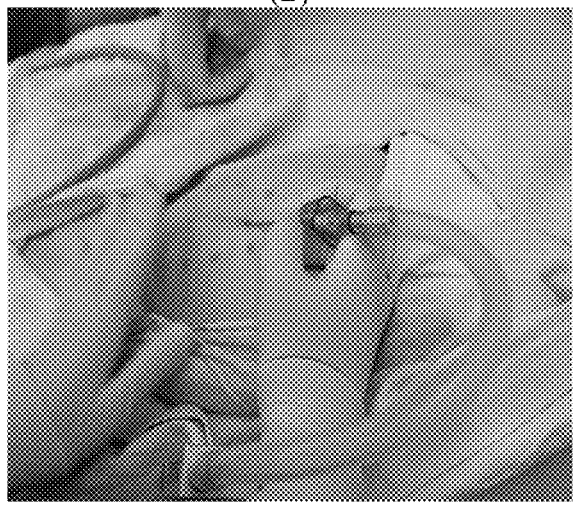
Figure 3:
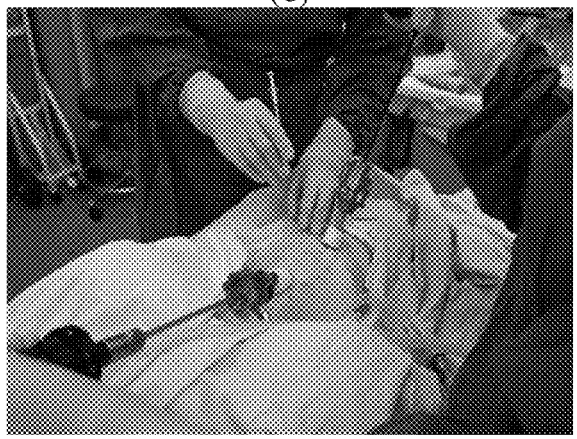

A 4-week pig (7 kg), after general anesthesia, was injected with $CO_2$ gas by inserting a veress needle into the abdominal wall. Then, a 5 mm laparoscopy trocar was inserted thereinto and the abdominal cavity structure of the pig was confirmed using a laparoscopy camera and a forceps (see FIG. 3).

Figure 4:
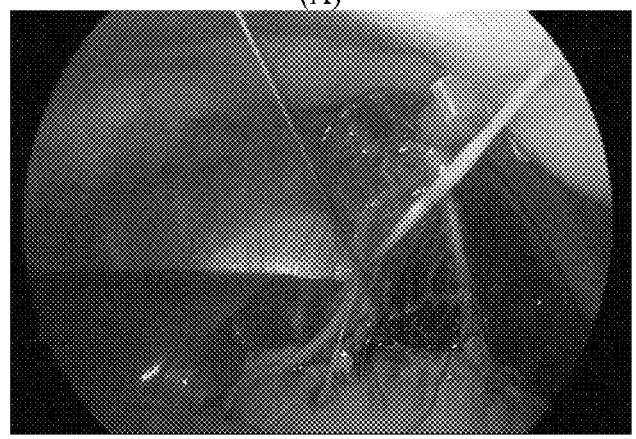
FIG. 4 shows the images of injecting the ovarian cancer cell line (SK-OV-3) into (A) the omentum, (B) the peritoneum, and (C) the uterine horn of a piglet in Example 1, respectively.
Figure 4:
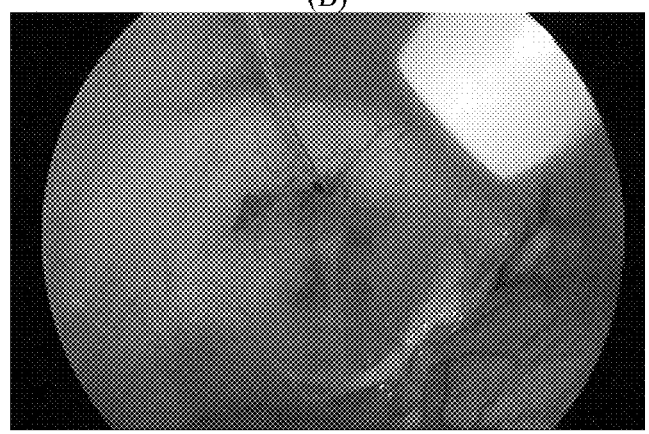
Figure 4:
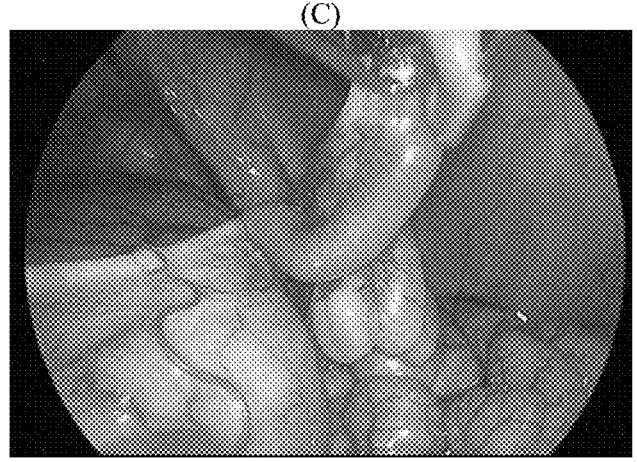

Then, 6 suspensions in an amount of 0.1 mL were prepared at a concentration of $5.0×10^6$ cells/0.1 mL, respectively, and to confirm the injection site, each suspension was mixed with 0.1% solution of indigocarmine and injected once to the fat tissue of the omentum, once to the submesothelial tissue of peritoneum at both sides and the uterine cavity within the uterine horn at both sides, respectively, for a total of 5 injections (see FIG. 4).

Figure 5:
FIG. 5 shows the images of (A) the omentum, (B) the peritoneum, and (C) the uterine horn of the piglet, one week after the injection of the ovarian cancer cell line (SK-OV-3) in Example 1, respectively; and the whitish inflammatory web, which occurred throughout (D) the peritoneum and (E) the small intestine of the piglet, respectively.
Figure 5:
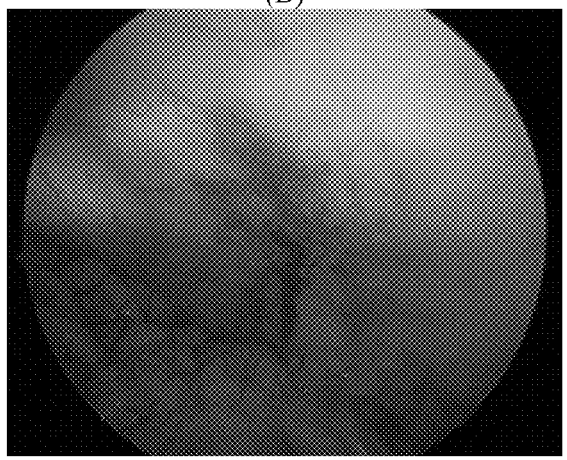
Figure 5:
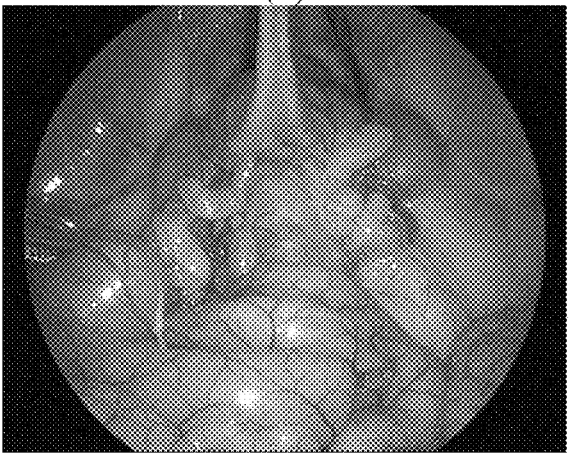
Figure 5:
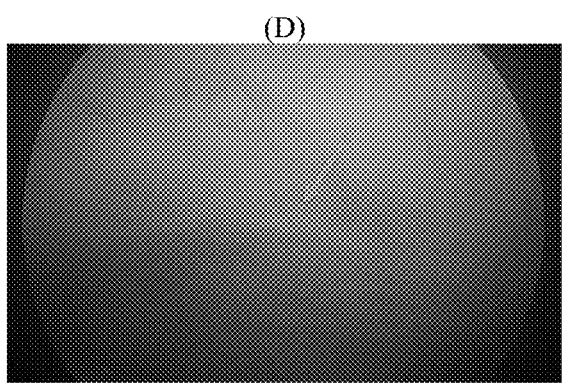
Figure 5:
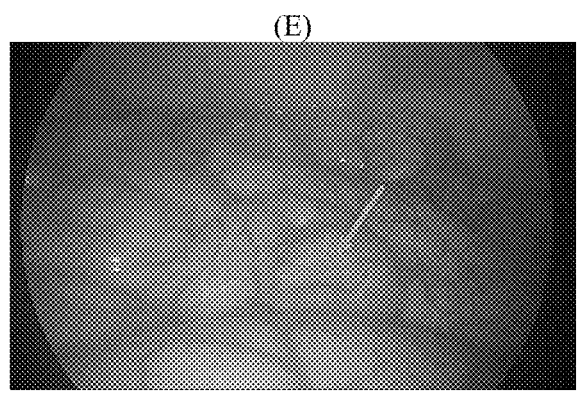

The presence of peritoneal carcinomatosis was examined one week thereafter, i.e., at the age of 5 weeks after birth (8 kg), using the laparoscopy, and there were no specific findings of the injection sites (i.e., omentum, peritoneum, and uterine horn). However, the occurrence of the whitish inflammatory web throughout the peritoneum and the small intestine was confirmed (see FIG. 5).

Five suspensions in an amount of 0.1 mL were prepared at a concentration of $5.0×10^6$ cells/0.1 mL, respectively, and to confirm the injection site, each suspension was mixed with 0.1% solution of indigocarmine and additionally injected once to the fat tissue of the omentum, the submesothelial tissue of peritoneum at both sides, and the uterine cavity within the uterine horn at both sides, respectively.

Figure 6:
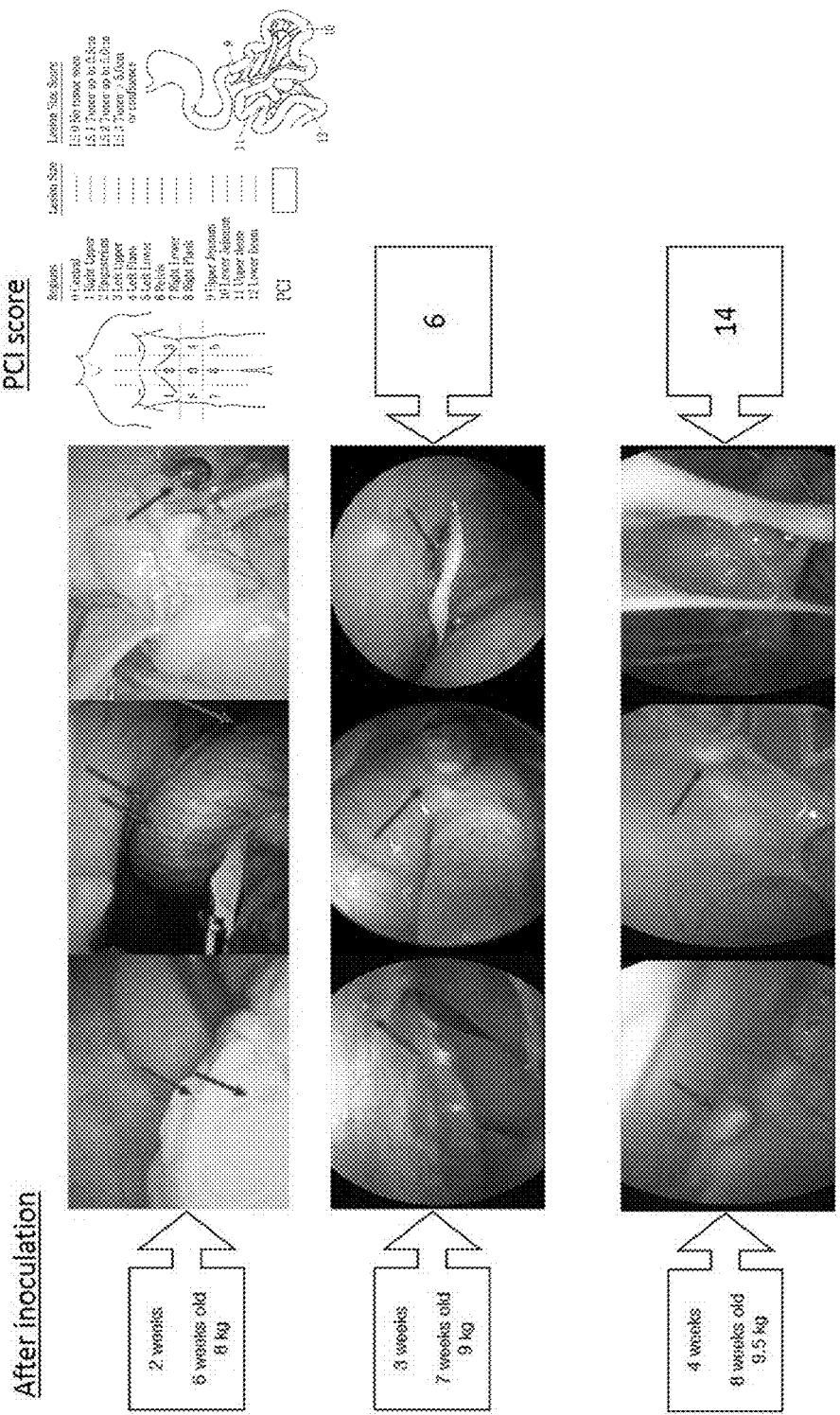
FIG. 6 shows the images of the progress of peritoneal carcinomatosis in the piglet, during the period from two weeks to four weeks after the injection of the ovarian cancer cell line (SK-OV-3) in Example 1, respectively.

FIG. 6 shows the images of the progress of peritoneal carcinomatosis in the piglet, during the period from two weeks to four weeks after the injection of an ovarian cancer cell line, respectively.

Referring to FIG. 6, at week 2, the metastasis of the upper and lower gastrointestinal tract tumors was confirmed, and it was confirmed that the uterine horn caused inflammation in the pelvic wall, thereby being adhered thereto and causing necrosis of the surrounding tissues.

At week 3, peritoneal carcinomatosis accompanying tumor metastasis and adhesion progressed, and the severity was evaluated by peritoneal carcinomatosis index (PCI) score.

Table 1 below shows a peritoneal carcinomatosis index (PCI) score for evaluating the severity of peritoneal carcinomatosis at 3 to 4 weeks after the inoculation of an ovarian cancer cell line.

TABLE 1

| Regions | Score (Week 3) | Score (Week 4) |
| --- | --- | --- |
| 0 Central | 0 | 2 |
| 1 Right Upper | 0 | 1 |
| 2 Epigastrium | 1 | 2 |
| 3 Left Upper | 0 | 1 |
| 4 Left Flank | 1 | 0 |
| 5 Left Lower | 2 | 1 |
| 6 Pelvis | 9 | 1 |
| 7 Right Lower | 1 | 3 |
| 8 Right Flank | 1 | 0 |
| 9 Upper Jejunum | 0 | 2 |
| 10 Lower Jujunum | 0 | 0 |
| 11 Upper Ileum | 0 | 1 |
| 12 Lower Ileum | 0 | 0 |
| Total | 6 | 14 |

As a result, a total PCI score of 6 PCI points were confirmed including the metastatic tumors in the peritoneum, intestine, uterine horn, etc. At week 4, peritoneal carcinomatosis and adhesion accompanying tumor metastasis became more severe, thereby confirming a total PCI score of 14 points.

In particular, there were findings that among the inoculation regions, the inflammation and metastasis of the uterine horn were preferentially progressed compared to the changes in the metastasis of the omentum and the peritoneum, and thus, the inoculation of the ovarian cancer cell line into the uterine cavity in the uterine horn is considered to be the most effective way to produce a large animal model with peritoneal carcinomatosis.

Example 2

In the method of Example 1, in order to select a method to maintain a continuous reaction between the uterine epithelial cells and the ovarian cancer cell line consistent by injecting a cell line at a sufficient concentration into the uterine cavity in the uterine horn to induce the tube shape using a piglet in which the immune function is not completed, and to reproduce the induction of peritoneal carcinomatosis in a large animal by this preparation method, an efficacy evaluation experiment was performed as follows.

Figure 7:
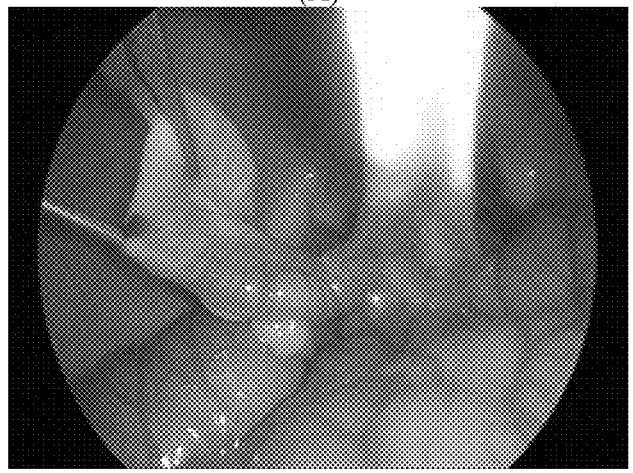
FIG. 7 shows the image of (A) the uterine horn of the piglet at the time of injection of the ovarian cancer cell line (SK-OV-3) in Example 2, and the images of the whitish inflammatory web occurred one week after the injection in (B) the small intestine and (C) the peritoneum of the piglet, respectively.
Figure 7:
Figure 7:
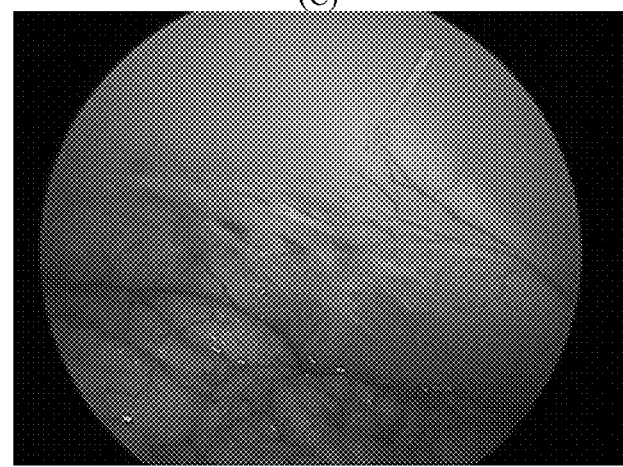

A 4-week pig (8 kg), after general anesthesia, was injected with $CO_2$ gas by inserting a veress needle into the abdominal wall. Then, a 5 mm laparoscopy trocar was inserted thereinto and the abdominal cavity structure of the pig was confirmed using a laparoscopy camera and a forceps. Then, a suspension (0.1 mL) at a concentration of $5.0 \times 10^6$ cells/0.1 mL of SK-OV-3 cell line was injected into the uterine cavity within the uterine horn at both sides, and the occurrence of the whitish inflammatory web throughout the peritoneum and the small intestine was confirmed one week thereafter, i.e., at the age of 5 weeks after birth (9 kg), and the suspension (0.1 mL) at a concentration of $5.0 \times 10^6$ cells/0.1 mL was re-injected into the uterine cavity within the uterine horn at both sides, respectively (see FIG. 7).

Figure 8:
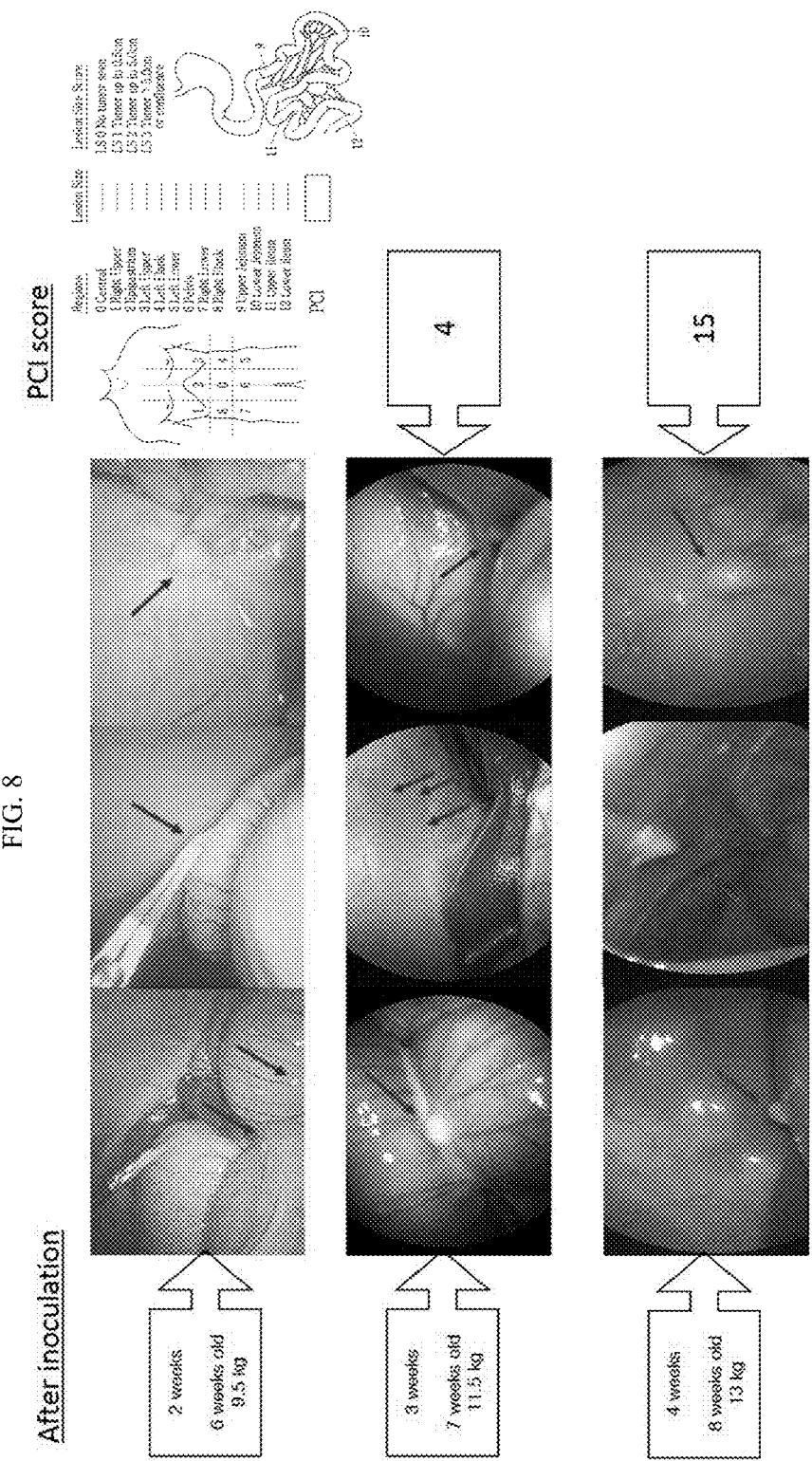
FIG. 8 shows the images of the progress of peritoneal carcinomatosis in the piglet, during the period from two weeks to four weeks after the injection of the ovarian cancer cell line (SK-OV-3) in Example 2, respectively.

At week 2, the metastasis of the upper and lower gastrointestinal tract tumors was confirmed, and it was confirmed that the uterine horn was adhered to the pelvic wall and tumor was formed. At week 3, peritoneal carcinomatosis accompanying tumor metastasis and adhesion progressed, and the severity was evaluated by peritoneal carcinomatosis index (PCI) score. As a result, a total PCI score of 4 PCI points were confirmed including the metastatic tumors in the peritoneum, intestine, uterine horn, etc. At week 4, peritoneal carcinomatosis accompanying tumor metastasis became more severe and the tumor size increased, thereby confirming a total PCI score of 15 points (see FIG. 8 and Table 2).

TABLE 2

| Regions | Score (Week 3) | Score (Week 4) |
| --- | --- | --- |
| 0 Central | 0 | 2 |
| 1 Right Upper | 0 | 0 |
| 2 Epigastrium | 0 | 0 |
| 3 Left Upper | 0 | 1 |
| 4 Left Flank | 1 | 2 |
| 5 Left Lower | 0 | 2 |
| 6 Pelvis | 1 | 2 |
| 7 Right Lower | 2 | 2 |
| 8 Right Flank | 0 | 0 |
| 9 Upper Jejunum | 0 | 2 |
| 10 Lower Jujunum | 0 | 2 |
| 11 Upper Ileum | 0 | 0 |
| 12 Lower Ileum | 0 | 0 |
| Total | 4 | 15 |

From the above, it was confirmed that the preparation method of a large animal model of peritoneal carcinomatosis of the present invention is reproducible and it was confirmed that the feature that the metastasis become serious was also similar.

Figure 9:
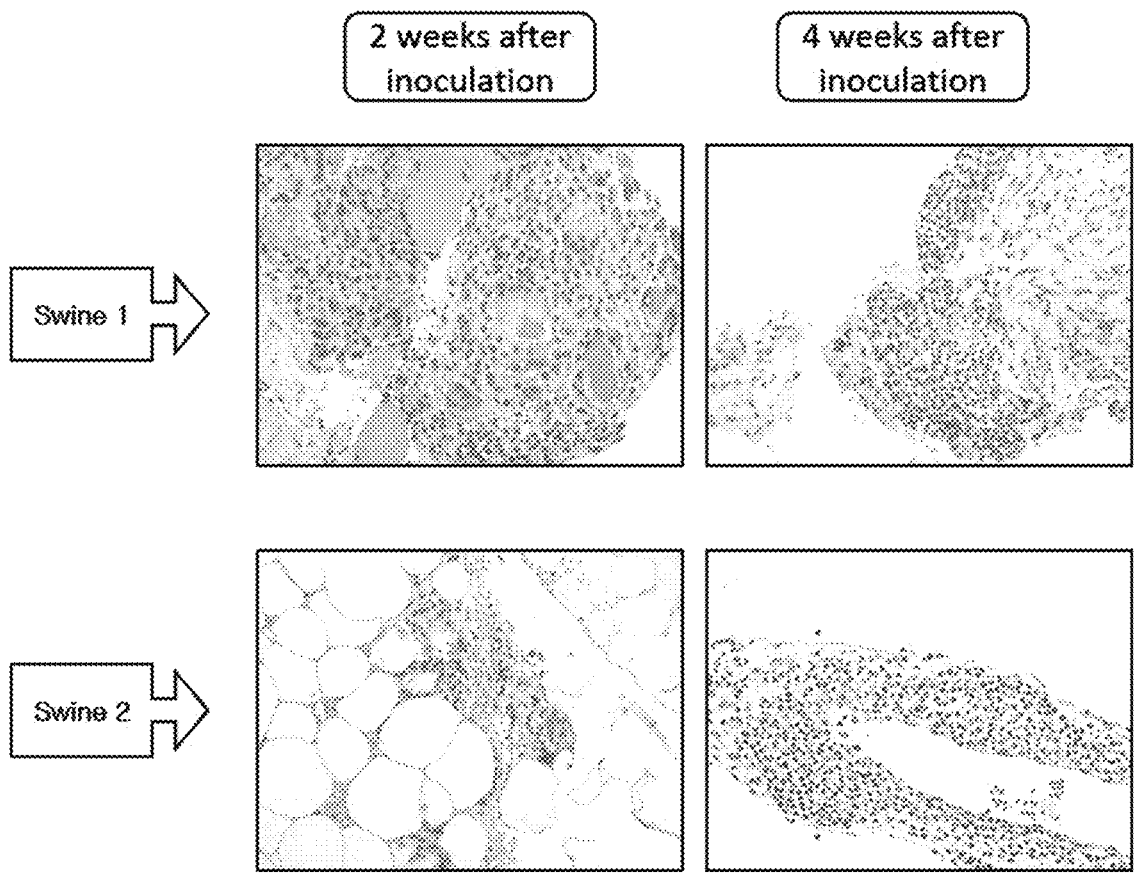
FIG. 9 shows the images of the infiltration of tumor cells in the metastatic tumor confirmed two weeks and four weeks after the injection of the ovarian cancer cell line (SK-OV-3).

Meanwhile, two weeks and four weeks after the ovarian cancer cell line injection, tissues were extracted from the areas where tumor metastasis was suspected to perform a histopathological examination, and as a result, the invasion of tumor cells as shown in FIG. 9 was observed in two pigs and that they were confirmed to be the same cell type.

Accordingly, two weeks after the injection of the ovarian cancer cell line, the development of tumor cells was demonstrated pathologically, and it was confirmed that this tumor was a metastatic tumor that progressed up to four weeks.

Example 3

Figure 10:
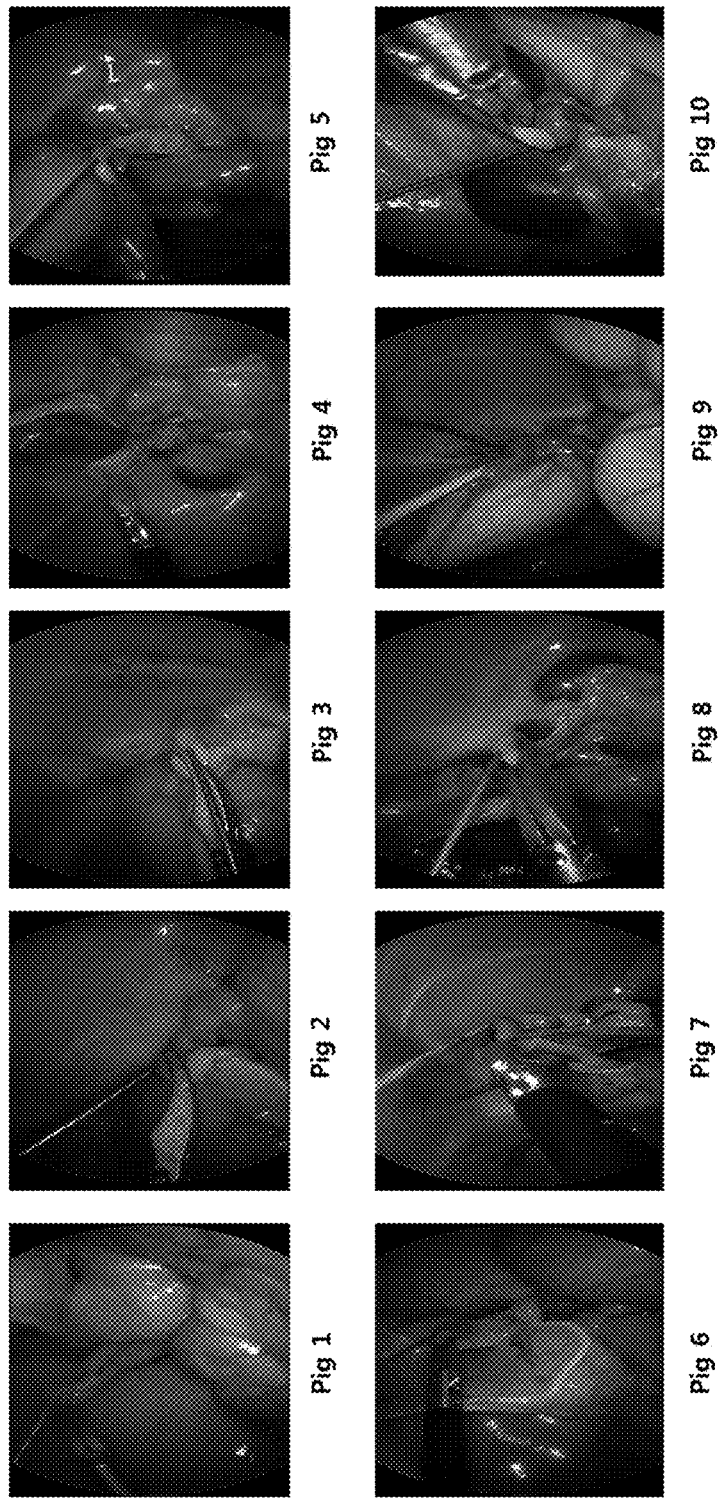
FIG. 10. shows the images of the uterine horn of ten 4-week piglets (7-8 kg) at (A) the first time of the injection of the ovarian cancer cell line (SNU-008); and (B) the second time of the injection of the ovarian cancer cell line (SNU-008) and (C) the whitish inflammatory web, which occurred throughout the peritoneum and the small intestine after one week in Example 3.

Then, a 4-week pig (7-8 kg), after general anesthesia, was injected with $CO_2$ gas by inserting a veress needle into the abdominal wall. Then, a 5 mm laparoscopy trocar was inserted thereinto and the abdominal cavity structure of the pig was confirmed using a laparoscopy camera and a forceps. Then, a suspension (0.1 mL) at a concentration of $5.0 \times 10^6$ cells/0.1 mL of SNU-008 cell line was injected into the uterine cavity within the uterine horn at both sides, and the occurrence of the whitish inflammatory web throughout the peritoneum and the small intestine was confirmed one week thereafter, i.e., at the age of 5 weeks after birth (8-9 kg), and the suspension (0.1 mL) at a concentration of $5.0 \times 10^6$ cells/0.1 mL of SNU-008 cell line was re-injected into the uterine cavity within the uterine horn at both sides, respectively (see FIG. 10).

Figure 11:
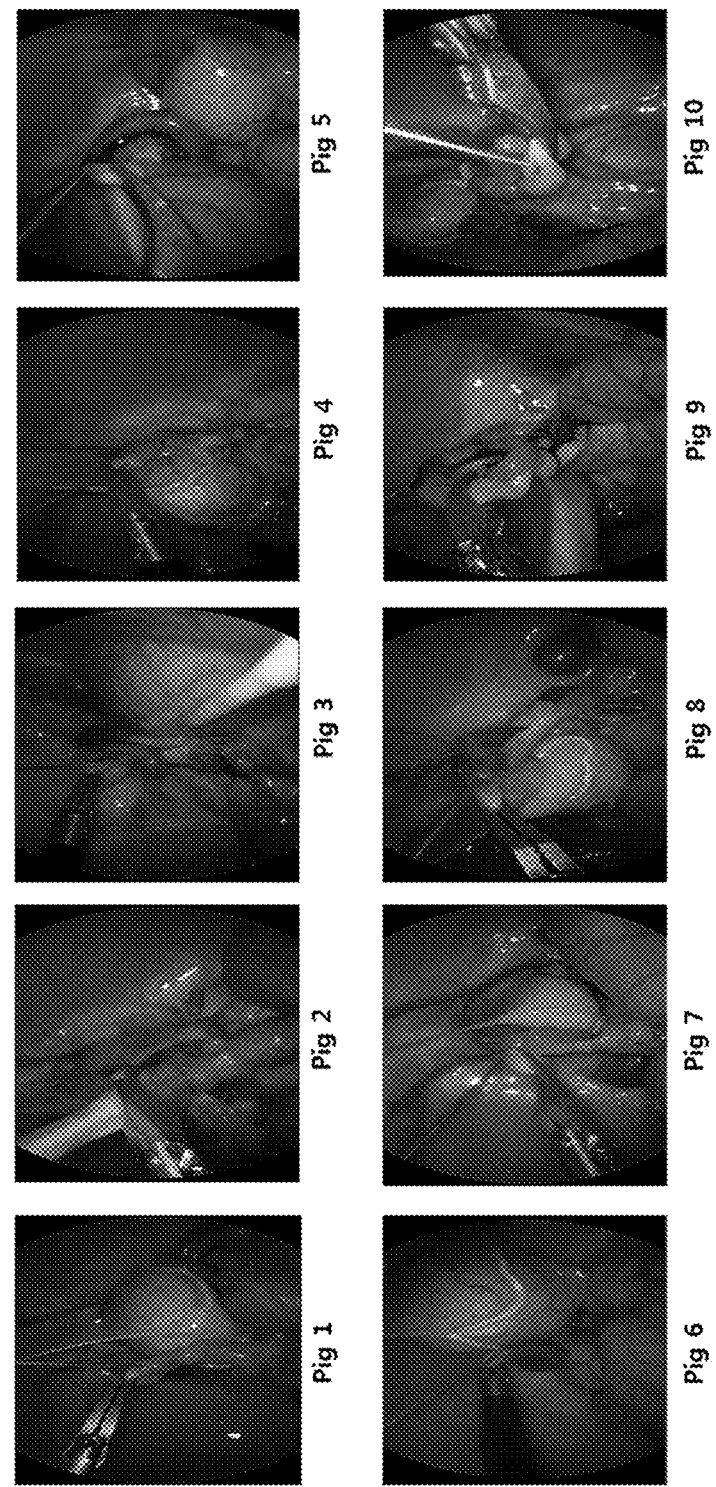
FIG. 11. shows the images of the progress of peritoneal carcinomatosis in seven piglets four weeks after the injection of the ovarian cancer cell (SNU-008) line in Example 3. Finally, the success for making a large animal model with peritoneal carcinomatosis was found in seven among ten piglets (70%)

At week 4, the metastasis in the abdominal cavity was confirmed, and it was confirmed that the uterine horn was adhered to the pelvic wall and tumor was formed. Peritoneal carcinomatosis accompanying tumor metastasis and adhesion progressed, and the severity was evaluated by peritoneal carcinomatosis index (PCI) score. As a result, total PCI scores ranged from 5 to 17 points, suggesting the success rate for making this model by using this preventing invention may be 70% and more (see FIG. 11 and Table 3).

TABLE 3

| Regions | Pig 1 | Pig 2 | Pig 3 | Pig 4 | Pig 5 | Pig 8 | Pig 10 |
| --- | --- | --- | --- | --- | --- | --- | --- |
| 0 Central | 3 | 2 | 2 | 3 | 1 | 3 | 3 |
| 1 Right Upper | 1 | 0 | 0 | 0 | 0 | 1 | 2 |
| 2 Epigastrium | 2 | 0 | 1 | 0 | 0 | 1 | 0 |
| 3 Left Upper | 1 | 1 | 0 | 0 | 1 | 0 | 0 |
| 4 Left Flank | 3 | 2 | 2 | 3 | 0 | 3 | 3 |
| 5 Left Lower | 3 | 0 | 0 | 0 | 0 | 1 | 3 |
| 6 Pelvis | 0 | 0 | 0 | 0 | 0 | 0 | 2 |
| 7 Right Lower | 0 | 0 | 0 | 0 | 1 | 0 | 0 |
| 8 Right Flank | 0 | 0 | 0 | 0 | 2 | 0 | 0 |
| 9 Upper Jejunum | 0 | 0 | 0 | 0 | 0 | 0 | 0 |
| 10 Lower Jujunum | 0 | 0 | 0 | 0 | 0 | 0 | 2 |
| 11 Upper Ileum | 1 | 0 | 0 | 0 | 0 | 1 | 0 |
| 12 Lower Ileum | 0 | 0 | 0 | 3 | 0 | 2 | 2 |
| Total | 14 | 5 | 5 | 9 | 5 | 12 | 17 |

The preferred embodiments of the present invention have been described in detail above, but the scope of the present invention is not limited thereto and various modifications and improvements of those skilled in the art using the basic concept of the present invention as defined in the following claims also belong to the scope of the present invention.

The method for preparing a large animal model with peritoneal carcinomatosis, when a human-derived immortalized cell line is inoculated into a pig, can overcome xenograft rejection and induce peritoneal carcinomatosis, can use animals with sufficient supply and demand, and can expect the spread of peritoneal carcinomatosis through breeding.

Especially, the success rate for making a large animal model with peritoneal carcinomatosis after the injection of the cancer cell line by using this present invention may range from 70% to 100%.

The large animal model prepared by the preparation method of a large animal model with peritoneal carcinomatosis is a large animal model closest to the human body, and even in a case where a cancer cell line derived from a human body is used, the treatment response can be analyzed by administering a drug via intravenous chemotherapy and intraperitoneal chemotherapy as in humans, instead of evaluating the treatment response by injecting a drug directly into the tumor or inducing a modification in the tumor growth environment, and it can also be used for the evaluation of a new medical technology using a surgery and medical device for the solid cancer of peritoneal carcinomatosis with a size comparable to that of humans.

What is claimed is:

1. A method for preparing a piglet with peritoneal carcinomatosis, comprising the step of
    (i) directly injecting $5.0 \times 10^6$ to $10.0 \times 10^6$ cells of a human ovarian cancer cell line into the uterine cavity within the uterine horn of a piglet in which the immune function is not completed, and
    (ii) re-injecting $5.0 \times 10^6$ to $10.0 \times 10^6$ cells of the human ovarian cancer cell line into the same site of the uterine cavity within the uterine horn of the piglet after one week of step (i) such that peritoneal carcinomatosis is produced in the piglet,
    thereby obtaining a piglet with peritoneal carcinomatosis and metastatic tumors in the peritoneum, intestine and uterine horn, and wherein the human ovarian cancer cell line is SK-OV-3 or SNU-008.

2. The method of claim 1, wherein the piglet in which the immune function is not completed is a 3- to 8-week-old pig with a body weight of 6 kg to 15 kg.

3. The method of claim 1, wherein the injecting the human ovarian cancer cell into the uterine cavity within the uterine horn is performed by using laparoscopy.

* * * * *